(12) United States Patent
Fandrey et al.

(10) Patent No.: US 9,689,759 B2
(45) Date of Patent: Jun. 27, 2017

(54) FIBER-OPTIC FORCE SENSOR, FORCE MEASUREMENT DEVICE AND CATHETER

(71) Applicant: VascoMed GmbH, Binzen (DE)

(72) Inventors: Stephan Fandrey, Affoltern am Albis (CH); Andreas Bitzer, Zurich (CH)

(73) Assignee: VascoMed GmbH, Binzen (DE)

( * ) Notice: Subject to any disclaimer, the term of this patent is extended or adjusted under 35 U.S.C. 154(b) by 705 days.

(21) Appl. No.: 13/974,615

(22) Filed: Aug. 23, 2013

(65) Prior Publication Data

US 2014/0081264 A1    Mar. 20, 2014

Related U.S. Application Data

(60) Provisional application No. 61/703,272, filed on Sep. 20, 2012.

(51) Int. Cl.
| | |
|---|---|
| *G02B 6/34* | (2006.01) |
| *G01L 1/24* | (2006.01) |
| *A61B 18/14* | (2006.01) |
| *A61B 5/00* | (2006.01) |

(52) U.S. Cl.
CPC .............. *G01L 1/246* (2013.01); *A61B 5/0084* (2013.01); *A61B 5/6885* (2013.01); *A61B 18/1492* (2013.01)

(58) Field of Classification Search
USPC ............................................................ 385/37
See application file for complete search history.

(56) References Cited

U.S. PATENT DOCUMENTS

| | | | |
|---|---|---|---|
| 5,399,854 A | 3/1995 | Dunphy et al. | |
| 2007/0112331 A1 | 5/2007 | Weber et al. | |
| 2007/0250036 A1 | 10/2007 | Volk et al. | |
| 2008/0285909 A1 | 11/2008 | Younge et al. | |
| 2009/0177095 A1* | 7/2009 | Aeby .................. | A61B 5/0084 600/478 |
| 2011/0066139 A1 | 3/2011 | Winegar | |
| 2012/0039358 A1* | 2/2012 | Bosselmann ......... | E21B 47/065 374/161 |
| 2012/0220879 A1 | 8/2012 | Fandrey et al. | |
| 2013/0096535 A1 | 4/2013 | Gregorich et al. | |

FOREIGN PATENT DOCUMENTS

| | | |
|---|---|---|
| EP | 2 777 479 A1 | 9/2014 |
| WO | 2008003307 | 1/2008 |
| WO | 2009007857 | 1/2009 |
| WO | 2009138957 | 11/2009 |

OTHER PUBLICATIONS

European Search Report and Annex to the European Search Report on European Patent Application No. EP 16 15 4007, dated Jul. 4, 2016 (9 pages).

* cited by examiner

*Primary Examiner* — Eric Wong
(74) *Attorney, Agent, or Firm* — Buchanan Ingersoll & Rooney PC

(57) ABSTRACT

A fiber-optic force sensor, comprising an FBG fiber that has a force sensor region, to which bracing means to eliminate or decouple laterally effective forces and bending moments are assigned in such a way that the force sensor has a predominantly single-axis response characteristic to detect merely the magnitude of a force acting axially in the fiber direction.

25 Claims, 4 Drawing Sheets

FIBER-OPTIC FORCE SENSOR, FORCE MEASUREMENT DEVICE AND CATHETER

CROSS-REFERENCE TO RELATED APPLICATIONS

This patent application claims the benefit of U.S. Provisional Patent Application No. 61/703,272, filed on Sep. 20, 2012, which is hereby incorporated by reference in its entirety.

TECHNICAL FIELD

The present invention relates to a fiber-optic force sensor, which comprises an FBG fiber that is mounted in a sensor holder and has at least one force sensor region. The present invention further relates to a force measurement device based on this force sensor principle and, lastly, to a catheter, in particular an ablation catheter, having a force sensor which is integrated in a distal portion and which is designed and arranged to measure the magnitude and the direction of an external force acting on the distal portion, wherein the force sensor is formed by a force sensor region on an FBG fiber.

BACKGROUND

In some fields of use of catheters or similar devices, for example electrode lines, a pressure on adjacent tissue is relevant to the function of said catheter or similar device, and therefore detection of this contact force is of interest. This is particularly true for what are known as ablation catheters, with which areas of tissue are ablated or tissue parts are removed.

An ablation catheter (e.g., "TactiCath" by Endosense) is known, which makes it possible to measure the magnitude and direction of a force, that is to say the aforementioned contact force in the case of application, acting on the distal catheter end during an ablation process. This catheter utilizes the principle of what is known as an FBG (Fiber Bragg Grating) sensor, wherein three fibers each with an FBG sensor at the end of the fiber form the group of sensors required for a 3D force measurement; it being possible to incorporate said sensors at a signal processing unit for joint measurement signal processing. The sensors are applied externally to a deformable cylinder at an angular distance of 120°.

In U.S. Publication No. 2008/0285909, the operating principle of FBG sensors for determination of torsions or curvatures of the catheter body is described in detail, and the operating principle of the aforementioned force sensor with a plurality of FBG fibers on a deformable cylinder is also explained in this document.

As described in International Publication No. WO 2009/138957, a temperature compensation is provided by means of three electric thermocouples, because even small temperature changes or deviations between the individual sensors can cause significant measurement uncertainties with the FBG measurement method and, with an electrothermal ablation process, rather considerable temperature fluctuations can occur at the tip of the ablation catheter.

The optical measurement principle of FBG sensor systems is known in general and, in particular, in its use for force measurements and temperature measurements; for example see "www.wikipedia.org/wiki/Fiber_Bragg_grating" or A. Othonos, K. Kalli: "Fiber Bragg Gratings: Fundamentels and Applications in Telecommunications and Sensing" Artec House 1999, and (specifically based on voltage and temperature measurements) U.S. Pat. No. 5,399,854. A detailed explanation of the measurement principle is understood by one of ordinary skill in the art and, therefore, is not necessary herein.

Irrespective of this measurement principle, other solutions for a contact force measurement on a guide wire or catheter are also known, for example with use of an optical sensor, as described in International Publication No. WO 2009/007857, or with use of a semiconductor sensor at the tip of a guide wire, as described in International Publication No. WO 2008/003307. A more recent solution is disclosed in U.S. Publication No. 2012/0220879, which also is owned by the present Applicant.

The present invention is directed toward overcoming one or more of the above-identified problems.

In view of the above-mentioned prior art, an object lies in specifying a force sensor that is suitable for simple applications and has particularly simple signal processing. A further object lies in specifying a force measurement device that is likewise simplified in terms of its signal processing and that is suitable for multi-axis force or pressure detection and corresponding applications. A further object lies in specifying a catheter that is of simple design and, therefore, can be produced cost effectively for specific applications, wherein patient safety is ensured to a high degree with use of said catheter.

SUMMARY

With regard to the force sensor, at least one of the stated objects is achieved by a force sensor having the features of claim 1. With regard to the force measurement device, at least one of the stated objects is achieved by a force measurement device having the features of claim 6. With regard to the catheter, at least one of the stated objects is achieved by a catheter having the features of claim 11. Expedient developments of the inventive concept are disclosed in the respective dependent claims.

The present invention is based on the knowledge that a specific combination of the force components acting in the three spatial directions is measured with each sensor region (depending on the angular position thereof relative to the FBG fiber) in the previously known single-fiber force sensor of simple design that can be produced with small dimensions. The sensitivity in the z-direction is much lower compared to lateral loads from the xy-direction due to the bending moments. With this design, it is not easily possible to increase the sensitivity of the z-direction without increasing the sensitivity in the xy-direction, whereby the sensor becomes too unstable from a certain point. The dynamic range of the FBG sensors therefore cannot be utilized optimally for the mechanical loads and, therefore, temperature influences in the system are always on a par with the mechanical load. Additional sensor regions are therefore necessary in order to achieve a suitable temperature compensation, thus increasing the complexity and costs of such a system.

Based on this knowledge, the present invention includes the consideration of producing a force sensor of the aforementioned type that is sensitive substantially only in the z-direction and, continuing this idea, of producing a force measurement device that comprises such a sensor component that is sensitive substantially in the z-direction. It is accordingly proposed for the FBG fiber to comprise a force sensor region assigned bracing means to eliminate or decouple laterally effective forces and bending moments in such a way that the force sensor region has a predominantly single-axis response characteristic to detect merely the magnitude of a force acting axially in the fiber direction.

In accordance with a further aspect of the present invention, in the sensor holder of an FBG fiber comprising three force sensor regions, bracing means for eliminating or decoupling laterally effective forces and bending moments are assigned to one of the three force sensor regions in such a way that the force sensor has a predominantly single-axis response characteristic for detecting merely the magnitude of a force acting axially in the fiber direction. In accordance with the latter aspect concerning a variably usable force measurement device, the remaining two force sensor regions are arranged on the FBG fiber, in particular with an angular offset of, for example, approximately 90°, in such a way that they are designed to detect the magnitude and the direction of the projection of the effective force onto the plane perpendicular to the extension of the FBG fiber.

In one embodiment of the proposed force sensor, the FBG fiber is arranged on a sensor holder which is resilient and flexible in some portions in the axial direction and which is assigned a bracing part that is displaceable axially relative to the sensor holder, but is not displaceable in a lateral direction. In one variant of this embodiment, the sensor holder is formed by an outer tube that is soft in some portions and the bracing part is formed by a hard inner tube, or the sensor holder is formed by an inner tube that is soft in some portions and the bracing part is formed by a hard outer tube, wherein the inner tube is guided axially and displaceably in the outer tube.

In an alternative embodiment, the FBG fiber is arranged on a sensor holder that is soft in the axial direction in the region of the force sensor region with a single-axis response characteristic, but is braced with respect to laterally effective forces and bending moments by at least two transverse struts inclined with respect to the longitudinal axis of the sensor holder, in particular, enclosing an angle between approximately 45° and 90° with the longitudinal axis. In accordance with a variant of this embodiment, the sensor holder has precisely two transverse struts in spatial assignment to the force sensor region, said transverse struts being connected at both ends by longitudinal struts, wherein the sensor holder has a portion deformable in the axial direction, both before the first transverse strut and after the second transverse strut, as viewed in the axial direction.

Corresponding embodiments also apply to the aforementioned force measurement device, namely, specifically with regard to the force sensor region with a predominantly single-axis response characteristic. These embodiments will not be repeated herein; however, it is noted that the respective sensor holder is substantially rigid in the axial direction in the portions in which the FBG fiber has force sensor regions sensitive in the x- and y-directions.

Embodiments of the proposed catheter are designed similarly, and these features will not be repeated again with regard to the catheter. Reference is made expressly, however, to the fact that catheters or catheter arrangements can be produced appropriately on the basis of the present invention, both with a force sensor having substantially purely axially sensitivity and with a force measurement device having a triple-axis response characteristic. In any case, the respective signal processing is simplified and, at least in expedient embodiments, the sensor configuration is also simplified as a result of the possible omission of temperature sensors or temperature sensor regions.

Further features, aspects, objects, advantages, and possible applications of the present invention will become apparent from a study of the exemplary embodiments and examples described below, in combination with the figures, and the appended claims.

DESCRIPTION OF THE DRAWINGS

Advantages and expedient features of the present invention will become clear from the following description of exemplary embodiments on the basis of the Figures, in which.

DETAILED DESCRIPTION

Figure 1:
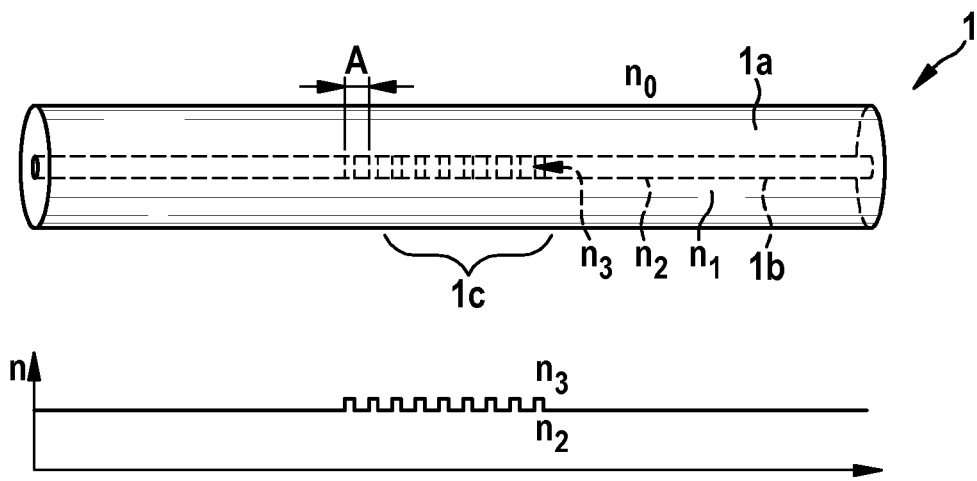
FIG. 1 shows a schematic diagram of the design of an FBG fiber.

The upper part of FIG. 1 shows a schematic, perspective illustration of a portion of an FBG fiber 1, which is embedded in a casing 1a with a refractive index $n_1$, and has a core 1b, of which the refractive index is $n_2$ substantially over the entire length of extension. A Bragg Grating, in which portions with the refractive index $n_2$ alternate with portions of another refractive index $n_3$, as illustrated in the lower part of FIG. 1, is formed in a sensor portion 1c of the fiber 1. The sensor portion 1c of the fiber 1 may be used inter alia to detect voltages and/or external force effects or temperature changes, as is known from the prior art and, therefore, is not described herein in greater detail.

In principle, to calculate a 3D force vector, the sensor system must be calibrated by subjecting the sensor successively to three forces (Fx, Fy, Fz) that are perpendicular to one another.

In theory, the strains $\epsilon_1$, $\epsilon_2$ and $\epsilon_3$ in the distributed sensor regions are calculated with the flexural rigidities E×I (with modulus of elasticity of the material and the corresponding elements of the flexural rigidity matrix), the bending moments F×l (with the corresponding force components and the respective fulcrum l of the bending moment) and the respective distance element $r_{ij}$ to the strain-neutral fiber, as well as the cross-sectional area A, which is subject to the axially effective force component, as follows:

$$\epsilon_1 = \frac{F_x \cdot l_1}{E \cdot I_{xx1}} \cdot r_{11} + \frac{F_y \cdot l_1}{E \cdot I_{yy1}} \cdot r_{12} + \frac{F_z}{A \cdot E} \qquad \text{Eq. (1)}$$

-continued $$\varepsilon_2 = \frac{F_x \cdot l_2}{E \cdot I_{xx2}} \cdot r_{21} + \frac{F_y \cdot l_2}{E \cdot I_{yy2}} \cdot r_{22} + \frac{F_z}{A \cdot E}$$

$$\varepsilon_3 = \frac{F_x \cdot l_3}{E \cdot I_{xx3}} \cdot r_{31} + \frac{F_y \cdot l_3}{E \cdot I_{yy3}} \cdot r_{32} + \frac{F_z}{A \cdot E}$$

A corresponding calibration matrix can be calculated as follows with three measurements, in which three forces perpendicular to one another can be used:

$$\begin{pmatrix} C_{11} & C_{12} & C_{13} \\ C_{21} & C_{22} & C_{23} \\ C_{31} & C_{32} & C_{33} \end{pmatrix} = \begin{pmatrix} F_x & 0 & 0 \\ 0 & F_y & 0 \\ 0 & 0 & F_z \end{pmatrix} \cdot \begin{pmatrix} \varepsilon_{11} & \varepsilon_{12} & \varepsilon_{13} \\ \varepsilon_{21} & \varepsilon_{22} & \varepsilon_{23} \\ \varepsilon_{31} & \varepsilon_{32} & \varepsilon_{33} \end{pmatrix}^{-1} \quad \text{Eq. (2)}$$

The flexural rigidities EI and distances to the neutral fiber r in the sensor holder have to be construed such that three linearly independent equations are given. It is this possible to calculate a 3D force vector from measured strains in any desired force direction with the aid of the following calibration matrix:

$$\begin{pmatrix} F_x \\ F_y \\ F_z \end{pmatrix} = \begin{pmatrix} C_{11} & C_{12} & C_{13} \\ C_{21} & C_{22} & C_{23} \\ C_{31} & C_{32} & C_{33} \end{pmatrix} \cdot \begin{pmatrix} \varepsilon_1 \\ \varepsilon_2 \\ \varepsilon_3 \end{pmatrix} \quad \text{Eq. (3)}$$

These calibration data are optionally stored in the catheter on, for example, an EEPROM, RFID or a 2D barcode and are read out by the evaluation unit either wirelessly or in a wired manner, or, with a 2D barcode, are read out optically.

Figure 2:
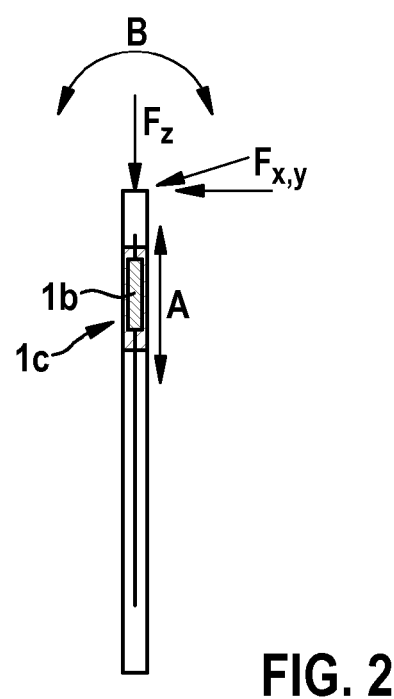
FIG. 2 shows a schematic illustration to explain the present invention.

To illustrate a key aspect of the present invention, FIG. 2 shows a schematic side view of a force sensor that is sensitive in the axial direction (z-direction) and that is braced in the event of a force acting in the xy-plane.

For the operating principle of the purely z-sensitive sensor, the highest possible flexural rigidity Ixx and Iyy for forces from the xy-direction and the lowest possible resistance for forces from the z-direction have to be achieved in accordance with Equation (1). As illustrated in FIG. 2 (as region A), the sensor region is soft in the z-direction and yields slightly with a force $F_z$. For forces from the x- and y-directions (illustrated symbolically by the double-headed arrow B), the sensor is braced such that an increased bending moment is provided in these directions.

Figure 3A:
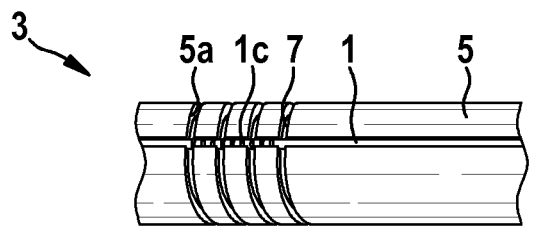
FIGS. 3A-3B show, respectively, a perspective detailed view and a longitudinal sectional illustration to explain an embodiment of the force sensor according to the present invention.
Figure 3B:
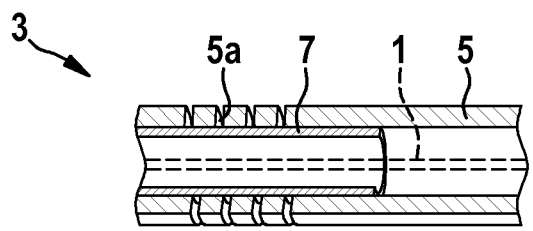

FIGS. 3A-3B show, respectively, a perspective view and a longitudinal sectional illustration of a portion of a force sensor 3 of substantially elongate cylindrical design, which, as a force measurement element, comprises an FBG fiber 1 having a sensor region 1c of the type shown in FIG. 1 and described further above. The FBG fiber 1 is mounted on an outer tube (sensor holder) 5 provided with a helical groove 5a by housing an inner tube (bracing part) 7 with a sliding fit relative to the outer tube 5.

In the event of forces acting substantially axially, the region of the outer tube 5, in which the helical groove 5a is incorporated, is resiliently soft and, therefore, the axial force component is introduced into the sensor region 1c in a largely unaltered manner. By contrast, the rigid inner tube 7 opposes a high bending moment perpendicular to the force components acting in the axial direction and, therefore, a flexural deflection of the sensor holder and, therefore, also of the FBG fiber 1 mounted thereon, is eliminated where possible. The force sensor 3 is therefore sensitive to forces acting in the axial direction (z-direction), but is substantially unresponsive to forces acting perpendicular thereto (x- and y-directions).

Figure 4A:
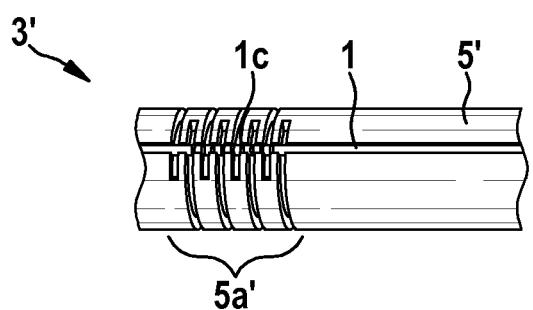
FIGS. 4A-4B show, respectively, a perspective detailed view and a longitudinal sectional illustration to explain a further embodiment of the force sensor according to the present invention.
Figure 4B:
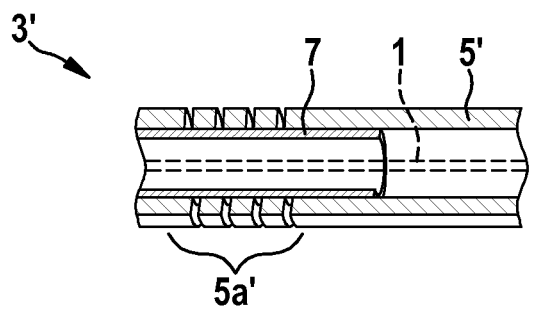

A force sensor 3' as shown in FIGS. 4A-4B functions in the same manner and is designed rather similarly to the sensor 3 according to FIGS. 3A-3B. It differs from the sensor 3 merely in that a portion 5a', in which incisions shaped as a sector of a circle are provided alternately in opposed circumferential regions of the sensor holder, is provided at the point of the helical groove 5a in the outer tube (sensor holder) 5', the ends of said incisions overlapping beneath the sensor region 1c of the FBG fiber 1. These alternating, overlapping incisions lend the outer tube (sensor holder) 5' a soft, resilient response characteristic, similarly to the helical groove in the aforementioned embodiment, and thus ensure the sensitivity of the force sensor 3' with respect to axially effective forces, while the rigid inner tube 7 ensures that the force sensor is not sensitive with respect to forces acting perpendicular to the longitudinal axis.

Both previously described embodiments of the force sensor 3, 3' can also be implemented in principle with a sensor holder and/or bracing element of deviating design, for example, with a sensor holder shaped in its entirety as a (plastics) helix and a triangular, tetragonal or polygonal bracing element, and also with swapping of the arrangement of the holder element and reinforcement element in such a way that the sensor holder is placed within the bracing element. With application of the force sensor in a catheter, the above-described elongate cylindrical design is advantageous, since it can be integrated advantageously into a flexible catheter tube, an electrode line, or the like.

Figure 5A:
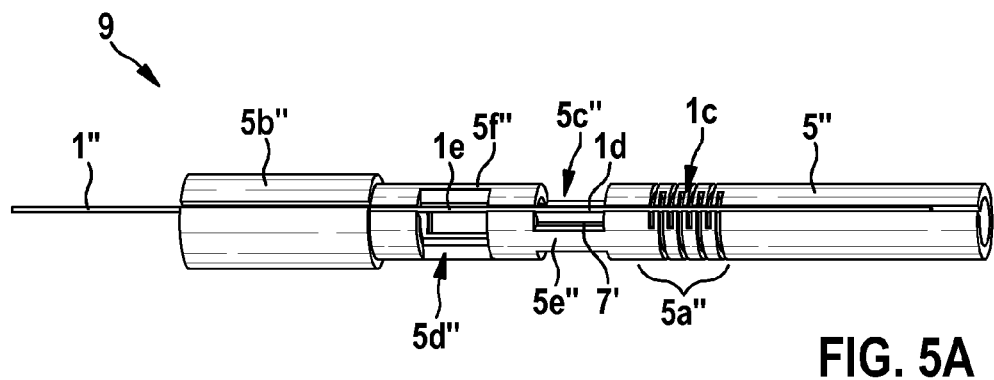
FIGS. 5A-5B show, respectively, a perspective illustration and a longitudinal sectional illustration of an embodiment of the force measurement device according to the present invention.
Figure 5B:
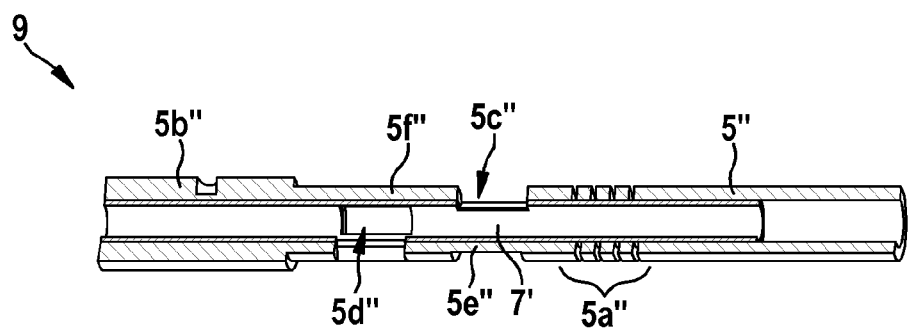

FIGS. 5A-5B show, respectively, a perspective view and a longitudinal sectional illustration of a force measurement device 9 which detects multi-axially (e.g., tri-axially) and utilizes the above-described operating principle of the force sensor sensitive uni-axially in the direction of the longitudinal axis, and specifically the embodiment thereof shown in FIGS. 4A-4B. Insofar as the force measurement device 9 contains parts or portions that can be seen in other Figures and have been described above, the reference numerals used in the other Figures or reference numerals based thereon area also used in FIGS. 5A-5B.

Numeral 1" denotes a modified FBG fiber, on which two further force sensor regions 1d, 1e are provided in addition to the force sensor region 1c detecting the force effect in the z-direction, with force components that are effective in the x- and y-directions being detected over said two further force sensor regions 1d, 1e thanks to a corresponding design of the sensor holder. The sensor holder (outer tube) denoted in this case by numeral 5" is practically identical in terms of its portion shown in the top-right corner in the Figures to the sensor holder 5' according to FIGS. 4A-4B, but has an opposed end 5b" that is braced by enlargement of the diameter and has two pairs of recesses 5c" and 5d", shaped as sectors of a circle, in the central region. Each of these pairs of recesses 5c" and 5d" comprises two mutually opposed recesses, between which two webs 5e", 5f" remain in each case, and which consequently have a high bending elasticity and a low bending moment in a respective preferred direction. Since the orientations of the recess pairs 5c" and 5d" are offset by approximately 90° with respect to one another, the respective directions of greatest flexibility are also rotated through approximately 90° with respect to one another and, therefore, both recess pairs together ensure that the FGB fiber 1" can detect force components within the xy-plane (that is to say perpendicular to the longitudinal axis of the sensor holder) by means of their force sensor regions 1*d* and 1*e* assigned spatially to the recesses.

Since the inner tube (bracing part), which is denoted in this case by reference numeral 7', also itself has recesses (not denoted specifically) at the location of the recess pairs 5*c*" and 5*d*", it likewise does not act in a bracing manner at those points at which there is high flexibility and, therefore, does not impede a largely unaltered detection of xy force components or bending forces acting on the FBG fiber 1". On the whole, a force measurement device having the aforementioned tri-axially ("3D") response behavior is provided together with the axial sensitivity produced by the force sensor region 1*c*.

In this system described herein, each sensor region can be set individually with an optimized sensitivity in terms of its force direction. The dynamic range of the FBG sensors can thus also be used optimally. By utilizing the entire dynamic range provided in the event of mechanical load, a much greater sensitivity with respect to the effect of a force compared to thermal influences can be achieved, which is why it is possible to dispense with temperature compensation. The complexity and costs of such a system can thus also be reduced.

Figure 6:
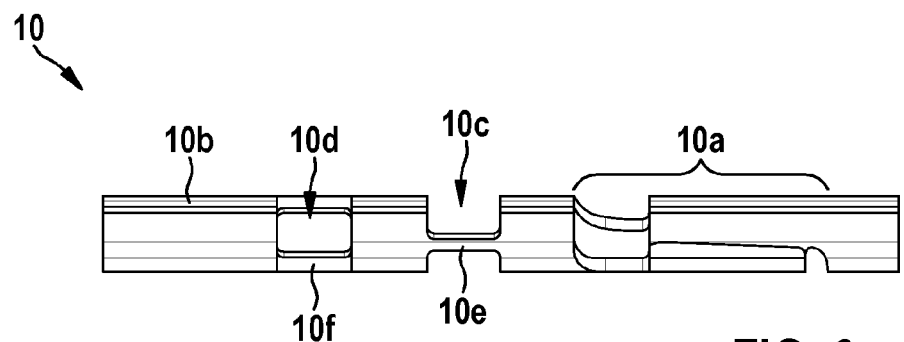
FIGS. 6-6A show, respectively, a longitudinal sectional illustration and a detail (side view) of a further embodiment of the force measurement device according to the present invention.

FIG. 6 shows a longitudinal sectional illustration of a one-piece sensor holder 10 of a further embodiment of the force measurement device according to the present invention (illustrated without an FBG fiber). Since the sensor holder 10 has certain similarities to the sensor holder (outer tube) 5" according to FIGS. 5A-5B, the individual portions are denoted based on these Figures and a further description is not necessary. Whereas, when an FBG fiber is mounted, the design of the part in which the x and y force sensor regions of said mounted FBG fiber are arranged coincides largely with the design of the sensor holder 5", and the portion 10*a*, which is formed specifically for detection of axially directed forces, is designed differently so as to dispense with the bracing part (inner tube) required in the previously described embodiment.

Figure 6A:
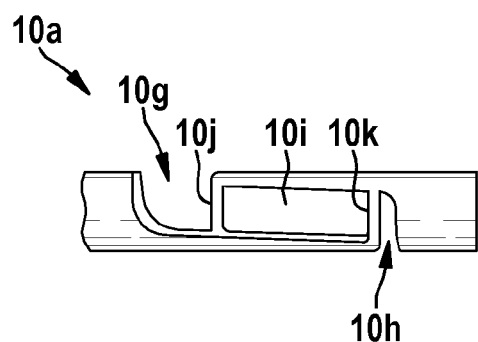

For improved clarification of the design of this portion, said portion is shown in FIG. 6A as a detail, again illustrated schematically, in a side view. FIG. 6A shows a view in the plane that is spanned by the longitudinal axis and the axis of the extent of the FBG fiber (not shown). As can be seen, its primary features are two deep incisions 10*g*, 10*h* in the sensor holder, which are introduced from opposite sides, and a continuous recess 10*i*, which is oriented at an angle of approximately 90° to both recesses 10*g*, 10*h*. Narrow webs 10*j*, 10*k* remain there between and form a type of parallelogram together with the remaining tube portions (not denoted specifically) of the sensor holder, which taper in opposite directions. This geometric design reacts softly and resiliently to axially effective forces, whereas radially acting forces (in the xy-plane) encounter high resistance through the webs 10*j*, 10*k*.

This design, which can be cut into a plastics tube by a laser, for example, enables a structurally simple and therefore cost-saving design of the sensor holder, in which certain disadvantages of the above-described two-part embodiments in terms of measurement accuracy can also be avoided.

Figure 7:
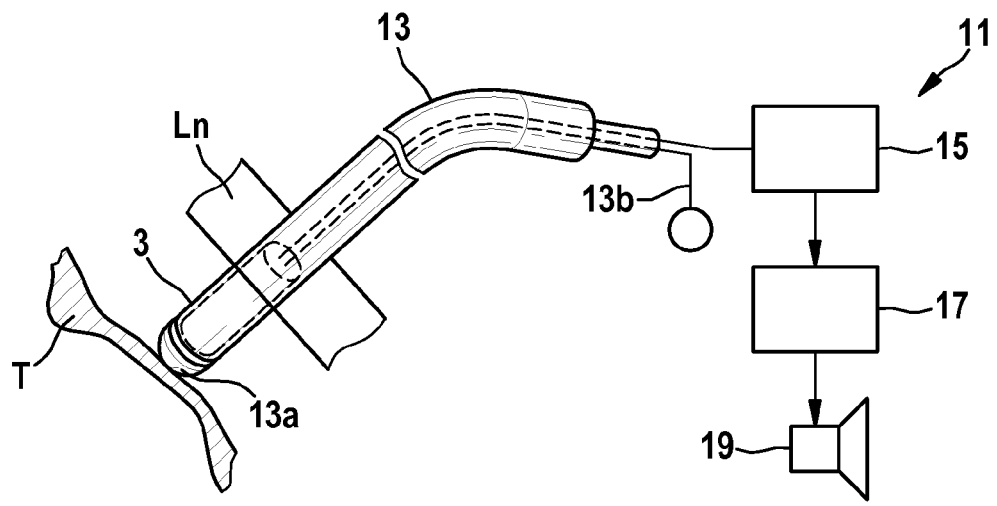
FIG. 7 shows a schematic illustration of a catheter arrangement according to the present invention.

FIG. 7 shows a schematic illustration of a catheter arrangement 11, which comprises an ablation catheter 13 with a point electrode 13*a*, in contact with a portion of bodily tissue T of a patient. In view of a prevailing risk of perforation of the bodily tissue T, the ablation catheter 13 is equipped with a force measurement device arranged in the distal end portion and denoted in the Figure (with reference to FIGS. 3A-3B) by numeral 3. This force measurement device is designed as a single-axis force sensor, in which substantially axially effective forces originating from contact with the tissue T are recorded via the resiliently mounted point electrode 13*a*. The proximal end of the force measurement device 3 is a "force-neutral" plane Ln, with which a pull wire 13*b* can engage to control the catheter. Designs without a pull wire of this type are also possible, however.

A force signal is tapped at the end of the ablation catheter and is fed to a signal processing unit 15. This is connected on the output side to a comparison unit 17, in which a comparison value of the prepared force signal is processed and a control signal is emitted to a warning device 19 (illustrated herein as a loudspeaker) if a dangerously high magnitude of the registered axial force is established. The doctor is thus informed of a prevailing risk of perforation due to the signals of the force sensor 3 and can react accordingly.

The embodiment(s) of the present invention are not limited to the above-described examples and highlighted features, but can also be implemented in a large number of modifications, which lie within the capabilities of a person skilled in the art.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. A fiber-optic force sensor, comprising:
a Fiber Bragg Grating ("FBG") fiber mounted in a sensor holder and having at least one force sensor region, to which bracing means to eliminate or decouple laterally effective forces and bending moments are provided at the at least one force sensor region, wherein the at least one force sensor region has a predominantly single-axis response characteristic to detect merely the magnitude of a force acting axially in the fiber direction.

2. The force sensor as claimed in claim 1, wherein the FBG fiber is arranged on a sensor holder which is resilient and flexible in portions in the axial direction and which is provided a bracing part that is displaceable axially relative to the sensor holder, but is not displaceable in a lateral direction.

3. The force sensor as claimed in claim 2, wherein the sensor holder is formed by an outer tube that is soft in portions and the bracing part is formed by a hard inner tube, or the sensor holder is formed by an inner tube that is soft in some portions and the bracing part is formed by a hard outer tube, wherein the inner tube is guided axially and displaceably in the outer tube.

4. The force sensor as claimed in claim 1, wherein the FBG fiber is arranged on a sensor holder that is soft in the axial direction in the region of the force sensor region with a single-axis response characteristic, but is braced with respect to laterally effective forces and bending moments by at least two transverse struts inclined with respect to the longitudinal axis of the sensor holder and enclosing an angle between 45° and 90° with the longitudinal axis.

5. The force sensor as claimed in claim 4, wherein the sensor holder has precisely two transverse struts in spatial assignment to the force sensor region, said transverse struts being connected at both ends by longitudinal struts, wherein the sensor holder has a portion deformable in the axial direction, both before the first transverse strut and after the second transverse strut, as viewed in the axial direction.

6. A force measurement device for measuring the magnitude and direction of a force acting on a mechanical part, said force measurement device comprising:
an individual FBG fiber fixed in a sensor holder, said FBG fiber comprising three force sensor regions, which are connected to inputs of a measurement signal processing device for joint measurement signal processing, wherein bracing means for eliminating or decoupling laterally effective forces and bending moments are provided at one of the three force sensor regions, wherein the force sensor has a predominantly single-axis response characteristic for detecting merely the magnitude of a force acting axially in the fiber direction, and wherein the remaining two force sensor regions are arranged on the FBG fiber with an angular offset of approximately 90° and detect the magnitude and the direction of the projection of the effective force onto the plane perpendicular to the extension of the FBG fiber.

7. The force measurement device as claimed in claim 6, wherein the three force sensor regions are formed in a spaced manner in the longitudinal direction of the FBG fiber, and the force sensor region with a predominantly single-axis response characteristic is arranged on a sensor holder which is resilient and flexible in portions in the axial direction and which is provided a bracing part that is displaceable axially relative to the sensor holder, but is not displaceable in a lateral direction.

8. The force measurement device as claimed in claim 6, wherein the FBG fiber is arranged on a sensor holder that is soft in the axial direction in the region of the force sensor region with a single-axis response characteristic, but is braced with respect to laterally effective forces and bending moments by at least two transverse struts inclined with respect to the longitudinal axis of the sensor holder and enclosing an angle between 45° and 90° with the longitudinal axis.

9. The force measurement device as claimed in claim 8, wherein the sensor holder has precisely two transverse struts in spatial assignment to the force sensor region with a single-axis response characteristic, said transverse struts being connected at both ends by longitudinal struts, wherein the sensor holder has a portion deformable in the axial direction, both before the first transverse strut and after the second transverse strut, as viewed in the axial direction, and is axially rigid in its further extent.

10. The force measurement device as claimed in claim 6, wherein the sensor holder has structurally predetermined mechanical weak points in the form of a spirally extending recess or a plurality of recesses shaped as sectors of a circle in a cylindrical holder housing, corresponding to the position of the force sensor regions.

11. A fiber-optic force sensor, comprising:
a Fiber Bragg Grating ("FBG") fiber mounted in a sensor holder and having at least one force sensor region for measuring force in an axial direction; and
a bracing part provided at the at least one force sensor region, wherein the bracing part is configured to eliminate or decouple laterally effective forces and bending moments acting on the fiber-optic force sensor at the at least one force sensor region,
wherein the at least one force sensor region has a predominantly single-axis response characteristic to detect merely the magnitude of a force acting axially on the FBG fiber direction.

12. The force sensor as claimed in claim 11, wherein the FBG fiber is arranged in the sensor holder which is resilient and flexible in the at least one force sensor region in the axial direction, and wherein the bracing part is displaceable axially relative to the sensor holder, but is not displaceable in a lateral direction.

13. The force sensor as claimed in claim 12, wherein the sensor holder is formed by an outer tube that is soft in the at least one force sensor region and the bracing part is formed by a hard inner tube, or the sensor holder is formed by an inner tube that is soft in the at least one force sensor region and the bracing part is formed by a hard outer tube, wherein the inner tube is guided axially and displaceably in the outer tube.

14. The force sensor as claimed in claim 11, wherein the FBG fiber is arranged in the sensor holder that is soft in the axial direction in the at least one force sensor region with a single-axis response characteristic, but is braced with respect to laterally effective forces and bending moments by at least two transverse struts inclined with respect to a longitudinal axis of the sensor holder and enclosing an angle between 45° and 90° with the longitudinal axis.

15. The force sensor as claimed in claim 14, wherein the sensor holder has precisely two transverse struts in spatial assignment to the at least one force sensor region, said precisely two transverse struts being connected at both ends by longitudinal struts, wherein the sensor holder has a portion deformable in the axial direction, both before the first transverse strut and after the second transverse strut, as viewed in the axial direction.

16. A force measurement device for measuring the magnitude and direction of a force acting on a mechanical part, said force measurement device comprising:
an individual Fiber Bragg Grating ("FBG") fiber fixed in a sensor holder, said FBG fiber comprising three force sensor regions, which are connected to inputs of a measurement signal processing device for joint measurement signal processing; and
a bracing part provided about one of the three force sensor regions, wherein the bracing part is configured for eliminating or decoupling laterally effective forces and bending moments acting on the force measurement device at the one force sensor region, wherein the force measurement device has a predominantly single-axis response characteristic for detecting merely the magnitude of a force acting axially in the FBG fiber direction, and wherein the remaining two force sensor regions are arranged on the FBG fiber with an angular offset of approximately 90° and are configured to detect the magnitude and the direction of the projection of the effective force onto the plane perpendicular to the extension of the FBG fiber.

17. The force measurement device as claimed in claim 16, wherein the three force sensor regions are formed in a spaced manner in a longitudinal direction of the FBG fiber, and the force sensor region with the predominantly single-axis response characteristic is arranged on a sensor holder which is resilient and flexible in portions in the axial direction and which is provided a bracing part that is displaceable axially relative to the sensor holder, but is not displaceable in a lateral direction.

18. The force measurement device as claimed in claim 16, wherein the FBG fiber is arranged in the sensor holder that is soft in the axial direction in the one force sensor region with a single-axis response characteristic, but is braced with respect to laterally effective forces and bending moments by at least two transverse struts inclined with respect to a longitudinal axis of the sensor holder and enclosing an angle between 45° and 90° with the longitudinal axis.

19. The force measurement device as claimed in claim 18, wherein the sensor holder has precisely two transverse struts in spatial assignment to the one force sensor region with the single-axis response characteristic, said precisely two transverse struts being connected at both ends by longitudinal struts, wherein the sensor holder has a portion deformable in the axial direction, both before the first transverse strut and after the second transverse strut, as viewed in the axial direction, and is axially rigid in its further extent.

20. The force measurement device as claimed in claim 16, wherein the sensor holder has structurally predetermined mechanical weak points in the form of a spirally extending recess or a plurality of recesses shaped as sectors of a circle in a cylindrical holder housing, corresponding to the position of the one force sensor region.

21. A catheter, in particular an ablation catheter, comprising:
a force sensor which is integrated in a distal portion of the catheter and which is designed and arranged to measure the magnitude and the direction of an external force acting on the distal portion, wherein the force sensor is formed by a force sensor region on an FBG fiber, to which bracing means to eliminate or decouple laterally effective forces and bending moments are provided at the force sensor region, wherein the force sensor region has a predominantly single-axis response characteristic to detect merely the magnitude of a force acting axially in the fiber direction.

22. The catheter as claimed in claim 21, wherein the FBG fiber is arranged on a sensor holder which is resilient and flexible in portions in the axial direction and which is provided a bracing part that is displaceable relative to the sensor holder, but is not displaceable in a lateral direction.

23. The catheter as claimed in claim 21, wherein the FBG fiber is arranged on a sensor holder that is soft in the region of the force sensor region with a single-axis response characteristic, but is braced with respect to laterally effective forces and bending moments by at least two transverse struts inclined with respect to the longitudinal axis of the sensor holder and enclosing an angle between 45° and 90° with the longitudinal axis.

24. A catheter, in particular an ablation catheter, comprising an integrated force measurement device as claimed in claim 6.

25. A catheter arrangement, in particular an ablation catheter arrangement, comprising a catheter as claimed in claim 21 and a signal processing unit connected thereto that has an individual input channel for the signals of the force sensors.

* * * * *